United States Patent [19]

List et al.

[11] 4,005,124

[45] Jan. 25, 1977

[54] PROCESS FOR RECOVERING THE MOTHER LIQUOR PRODUCED BY THE ESTERIFICATION OF TEREPHTHALIC ACID WITH METHANOL

[75] Inventors: Ferdinand List, Marl; Wilfried Uhlenbrock, Bochum; Norbert Wilke; Kurt Wember, both of Marl, all of Germany

[73] Assignee: Chemische Werke Huls Aktiengesellschaft, Marl, Germany

[22] Filed: Nov. 20, 1974

[21] Appl. No.: 525,516

[30] Foreign Application Priority Data

Nov. 28, 1973 Germany .......................... 2359199

[52] U.S. Cl. .......................................... 260/475 R
[51] Int. Cl.² .......................................... C07C 69/82
[58] Field of Search .............................. 260/475 R

[56] References Cited
UNITED STATES PATENTS 3,076,019  1/1963  Baldwin ...................... 260/945 R

*Primary Examiner*—Anton H. Sutto
*Attorney, Agent, or Firm*—Gilbert L. Wells

[57] ABSTRACT

The process of recovering methanolic mother liquor obtained by the esterification of terephthalic acid with methanol, where the terephthalic acid may be unprepurified, is improved by adjusting to a specific gravity of about 0.85 − 0.98 by addition of water and/or methanol distillate, a mother liquor containing esterification water and dissolved solids at a concentration of about 1.0 to 6.0 percent by weight and cooling the mother liquor from a temperature of about 65° − 85° C to a temperature of about 10° − 30° C to separate the solids and remove the separated solids. The separated solids may be recycled into the esterification reaction and the unseparated solids may be recycled for oxidation to terephthalic acid following distillation to remove the methanol.

23 Claims, 1 Drawing Figure

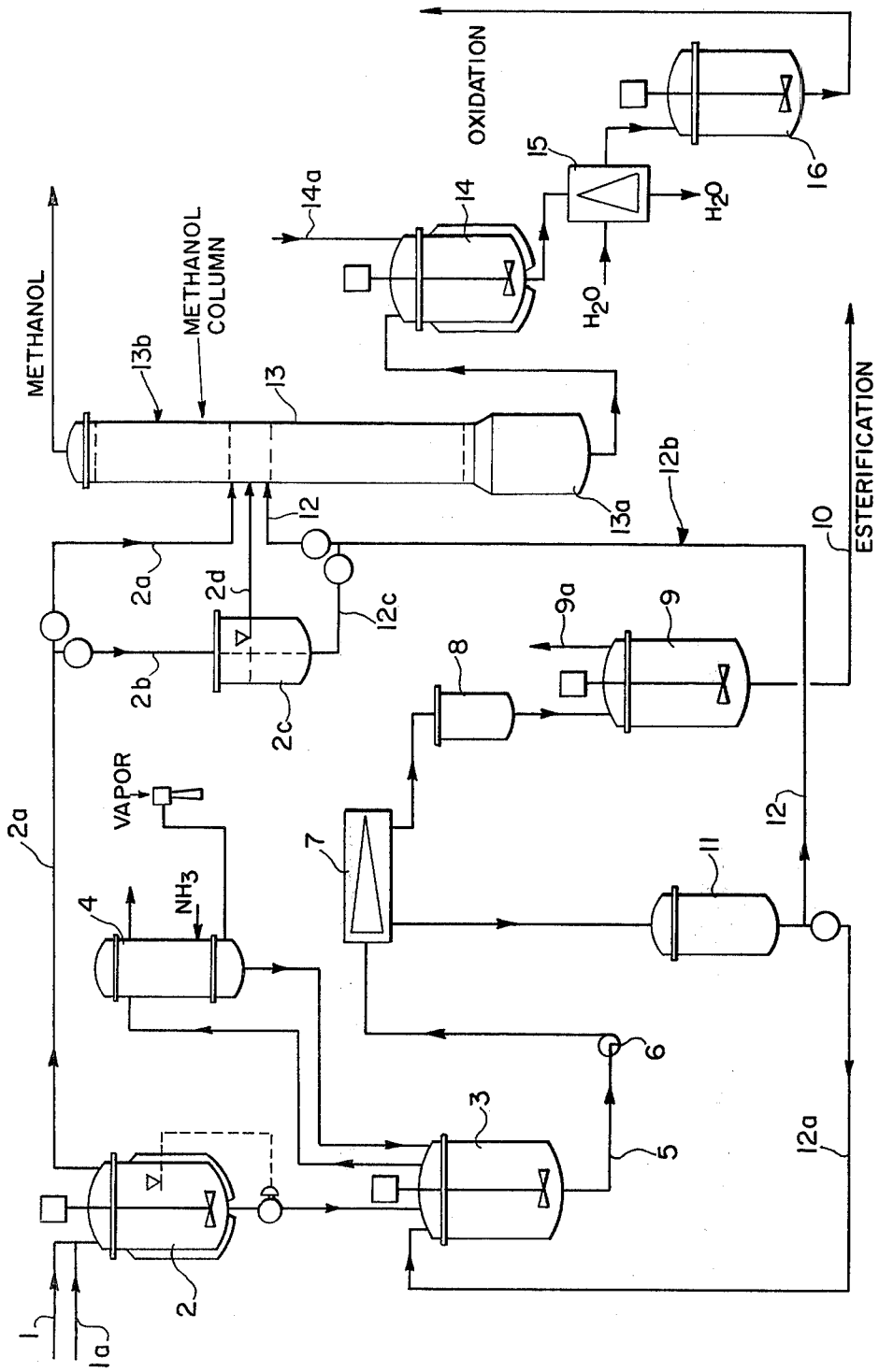

PROCESS FOR RECOVERING THE MOTHER LIQUOR PRODUCED BY THE ESTERIFICATION OF TEREPHTHALIC ACID WITH METHANOL

CROSS REFERENCES TO RELATED APPLICATIONS

Applicants claim priority under 35 U.S.C. 119 for Application P 23 59 199.3, filed Nov. 28, 1973 in the Patent Office of the Federal Republic of Germany.

The disclosures of assignee's copending U.S. Applications Ser. Nos. 39,761; 361,597, now U.S. Pat. No. 3,940,431; 364,085, now U.S. Pat. No. 3,886,200; 389,793, now U.S. Pat. No. 3,907,709; and 420,307, filed respectively May 22, 1970; May 18,1973; May 25, 1973; Aug. 29, 1973; and Nov. 29, 1973 are incorporated herein.

These copending applications disclose the state of the art of preparing dimethyl terephthalate by the esterification of terephthalic acid with vapor phase methanol.

BACKGROUND OF THE INVENTION

The field of the invention is esters and processes of making the same from polycarboxylic acids. The present application is particularly concerned with a process for recovering the methanolic mother liquor (ML) obtained in the preparation of dimethyl terephthalate (DMT) when possibly unprepurified terephthalic acid (TPA) is esterified with methanol (M).

The state of the art of preparing dimethyl terephthalate may be ascertained by reference to the Kirk-Othmer "Encyclopedia of Chemical Technology", 2nd Ed., Vol 15 (1968), pages 466–467, under the section "Current Commerical Processes for Polymer-Grade Dimethyl Terephthalate", and by reference to U.S. Pat. Nos. 2,876,252; 3,364,251; 3,399,227; 3,546,283; 3,607,044; and 3,617,226; and British Pat. Nos. 938,318; 1,043,289; and 1,053,164, the disclosures of which are incorporated herein.

Dimethyl terephthalate (DMT) is the raw material for the preparation of polyesters and especially for fibers, and because of this it is required to be of extremely high purity. On the other hand, commerical TPA generally also contains minute amounts of intermediate and side products. For instance, if TPA is prepared in known manner from p-xylol by air oxidation in the presence of heavy metal salts and bromine ions into acetic acid solution, then it contains slight amounts of impurities in the form of acetic acid (HAc), p-toluylene acid (TA), terephthal aldehyde acid (TPAA), benzoic acid (BA), p-hydroxymethylbenzoic acid, heavy metal salts, etc. Purification of the practically unmeltable and insoluble TPA is difficult. This applies most of all to separating the TPAA's. It was proposed in the prior art to apply air oxidation again for the crude TPA's in HAc at high temperatures above 200° C. However, the oxidizing decay of the HAc's and corrosion are interfering in this respect and also the leaching out of the crude TPA's with HAc, possibly followed by catalytic hydrogenation and/or carrier vapor sublimation are quite unsatisfactory because of the large cost in equipment and because recovery of the mother liquor obtained by esterifying the TPA's to DMT is still required.

Therefore immediate esterification of the crude TPA's with methanol was proposed. When this is done, the aldehyde components must be removed from the DMT, which is feasible only by means of costly purification, for instance by mixing the crude DMT with a compound containing a reactive methylene group, for instance ethylacetoacetate, diethyl malonate, ethylcyanoacetate, phenylbenzylketone, etc., by heating in the presence of an alkaline catalyst and separation by distillation of the purified DMT from the aldehyde condensation products as disclosed in British Pat. No. 938,318. Also, the crude ester contaminated mostly with terephthalaldehyde acid methyl ester has been treated with molecular oxygen in the melt in the presence of a catalyst soluble in the reaction system, this ester subsequently being separated from the oxidized contaminations by distillation as disclosed in British Pat. No. 1,043,289. The expenditures involved in puifying crude DMT when carrying out this process on an industrial scale are described in Europ. Chem. News of Sept. 29, 1972, 32: where the crude ester is distilled, then recrystallized twice and distilled again (see also Chemie Ing. Technik, 35 193 ff (1963), No. 3).

The above listed major difficulties in the preparation of pure DMT may be easily circumvented if the esterification of powdery crude TPA is carried out with methanol in the vapor state in the presence of bulk esterification catalysts such as silica gel beads, as disclosed in U.S. Pat. No. 3,607,044 and U.S. Pat. No. 3,907,709, for instance in conformity with the process of U.S. Pat. No. 3,617,226 and U.S. patent application Ser. No. 39,761, and U.S. patent application Ser. No. and U.S. Pat. Nos. 3,940,431 and 3,886,200. In this process, the product flow of methanol, DMT, MMT, (monomethyl terephthalate), $H_2O$, TPAA methylester, TA methylester, BA methylester, etc. issuing from the esterification reactor is cooled stepwise, whereby one obtains a suspension of finely crystallized DMT in boiling $CH_3OH$. That is, the more easily soluble intermediary products such as TPAA methylester, MMT, TA methylester, BA methylester etc. are dissolved from the crystallizate and enriched in the mother liquor under the conditions of a steady recrystallization or new dissolution.

Esterification under thos conditions takes place within a few seconds, and the thermal loading of the reaction products thereby is slight. Therefore, the crude ester is of outstanding quality because of the additional steady recrystallization. The terminal purification of this crude ester even in the presence of an initial acid with high concentrations of imtermediary and side products requires merely another simple distillation. However, serious difficulties are encountered in recovering a mother liquor containing DMT as well as intermediate and side products both as regards the recovery of the pure methanol as the recovery of the valuable end and intermediate products. This applies especially to a mother liquor of the above esterification containing from about 1.0 to 6.0 percent solids in solution besides water and minor amounts of methylacetate following separation of the crystallized out DMT at a temperature of 10° C, these dissolved solids being mostly DMT, MMT, TPAA merthylester, TA methylester and BA methylester. If this methanolic solution is subjected to recovery by distillation, appreciable complications are encountered: For instance the aldehyde compounds suffer from condensation reactions accompanied by the formation of products dyed markedly yellow and of no application (yellow oils). The necessary saponification of methylacetate yields acetic acid, so that high grade steel must be used. The occurrence of crystal sludge in the distillation sump and the crystallization out of DMT in the distillation column interfere with the recovery of the crystal sludge, which consists of various products, and causes apreciable cost expenditures.

These prior art problems are also described in U.S. Pat. No. 3,399,227, which recommends discarding the distillation resdiues.

U.S. Pat. No. 3,546,283 first teaches a commercially applicable process for recovering the mother liquor by saponifying the ester contained therein, by distilling off the methanol, by acid separation of the organic acids and their renewed use in the oxidizing stage. It is advantageous in this respect that ordinary steel equipment may be used, that the recovery of the substances dissolved in the mother liquor (oxidation end and intermediary products) appreciably increases the yield of the overall process, and that the interfering side-products are eliminated from the process. But there is the drawback of continued use of alkali and corresponding amounts of mineral acid.

SUMMARY OF THE INVENTION

Having in mind the limitations of the prior art, an object of the present invention is the recovery-processing of the mother liquor while keeping the already achieved advantages but essentially avoiding the use of alkali and acid.

The present invention achieves this objective by adjusting the density of a mother liquor containing esterification water and dissolved solids from about 1.0 to 6.0 percent by weight of the addition of water and/or by distilling off methanol, and by cooling the solution from a temperature between about 65° and 85° C down to about 10°–30° C, by separating the eliminated solids and if desired, in returning the latter into the esterification stage as well as the substances remaining dissolved following distillation of methanol into the oxidation process to terephthalic acid.

A suitable mother liquor is obtained by esterifying TPA, which need not be prepurified, and which may have been prepared from p-xylol by oxidation in air in the presence of heavy metal salts and bromine ions in acetic acid solution, with an excess of methanol, for instance by the above mentioned process in a reaction between powdered TPA and methanol vapors, and by separating thereupon the crystalline DMT from the esterification mixture.

Such a mother liquor cooled to about 10°–30° C contains from about 5 to 15, especially from 7 to 13 percent by weight water and about 1.0 to 6.0, especially 2.5 to 4.5 percent by weight dissolved solids, mostly DMT, MMT and the methylesters of TPAA, TA, BA and HAc besides traces of TPA and heavy metal salts. If the mother liquor contains less than 7 percent by weight, then it will be necessary to add a supplemental amount of water prior to the recovery process.

In general, the mother liquor treatable by this invention has the following composition range in weight percent:

|  | Preferred | Especially | Range |
| --- | --- | --- | --- |
| Methanol | 88.73 | 82.5–90.5 | 79–94 |
| Water | 7.50 | 7–13 | 5–15 |
| Terephthalic acid dimethyl ester | 0.45 | 0.35–0.90 | 0.20–1.20 |
| Terephthalic acid mono methyl ester | 1.85 | 1.20–1.90 | 0.30–1.90 |
| Terephthaldehydic acid methyl ester | 0.70 | 0.40–0.70 | 0.15–0.90 |

-continued

|  | Preferred | Especially | Range |
| --- | --- | --- | --- |
| Toluic acid methyl ester | 0.20 | 0.16–0.20 | 0.08–0.48 |
| Benzoic acid methyl ester | 0.02 | 0.02–0.25 | 0.01–0.48 |
| Acetic acid methyl ester | 0.05 | 0.02–0.05 | 0.01–0.06 |
| Unknown | 0.50 | 0.35–0.50 | 0.25–0.98 |
|  | 100.00. |  |  |

In general, the solids separated from the mother liquor by cooling precipitation according to the present invention have the following composition range in weight percent:

|  | Preferred | Especially | Range |
| --- | --- | --- | --- |
| Terephthalic acid (plus esters) | 96.7 | 96.2–99 | 93.5–99.8 |
| Terephthaldehydic acid methyl ester | 2.1 | 0.7–2.2 | 0.05–3.3 |
| Toluic acid methyl ester | 0.4 | 0.1–0.6 | 0.07–1.2 |
| Benzoic acid methyl ester | 0.4 | 0.15–0.5 | 0.05–1.0 |
| Unknown | 0.4 | 0.05–0.5 | 0.03–1.0 |

In general, the twice separated mother liquor resulting from the cooling precipitation according to the present invention has the following composition range in weight percent:

|  | Preferred | Range |
| --- | --- | --- |
| Methanol | 49.0 | 21.0–72.6 |
| Water | 49.0 | 22.4–77.0 |
| Terephthalic acid (plus esters) | 0.67 | 0.20–1.5 |
| Terephthaldehydic acid (plus ester) | 0.85 | 0.15–0.9 |
| Benzoic acid (plus ester) | 0.28 | 0.14–1.5 |
| Toluic acid (plus ester) | 0.12 | 0.10–1.3 |
| Intermediate runs | 0.02 | 0.01–0.4 |
| Last run (3 compounds) | 0.04 | 0.01–0.4 |
| Heavy metal | 0.02 | 0.01–0.4 |

Water is then added with stirring or rotating and with constant control of the water concentration to the apropriately heated mother liquor until the proper proportion of water between about 7 and 13 percent has been set and until simultaneously a specific gravity from about 0.85 to 0.98, preferably between 0.88 and 0.95, and especially between 0.90 and 0.93 has been achieved. Under these conditions and at a temperature between about 65° and 85° C, especially between 70° and 80° C, a preferred clear solution is obtained.

A preferred process for enriching the mother liquor with water consists in evaporating enough methanol that between 65° and 85° C, especially between 70° and 80° C, a preferred solution is obtained with a specific gravity of about 0.85 to 0.98, preferably from 0.88 to 0.95, especially from 0.90 to 0.93, which is just clear. The advantage of this method consists in handling relatively small reaction volumes in the ensuing process stages and in that no additional water need be heated in the methanol recovery by distillation.

The object of both process variations, which may be combined if desired, is to so adjust the water concentration in the hot solution that it will suffice for the subsequent separation of a given part of the dissolved constituents and independently of the amount of reaction water contained initially and as a function of the molar esterification ratios of the mother liquor. The assumption is that the water content of the mother liquor will be at least 7 percent. If it were less, then the above required specific gravity values are obtained in evaporating methanol only by practically completely concentrating the mother liquor. Then the separation into two different groups of the dissolved constituents, which is the purpose of the ensuing steps, could not be effected.

It is also important that the hot mother liquor be set for the required specific gravity values by adding water and/or distilling off methanol. If for instance the specific gravity is less than 0.90, then following cooling of the solution, increasing proportions of the constituents remain dissolved. If on the other hand the specific gravity exceeds 0.93, an increasinly fine-grained crystallizate is obtained, which settles relatively slowly. Above 0.97, the precipitate will float and for instance may no longer be separated and washed by centrifugally removing the solid from a liquid, for instance by solid jacket centrifuges. By observing the proper value of specific gravity, a very precise control of precipitation is easily achieved.

With respect to flawless recovery of the mother liquor enriched with water and possibly concentrated, it is further advantageous that the dissolved constituents be of concentrations not exceeding 15 percent by weight. During the ensuing cooling, higher concentrations result in precipitating constituents as voluminous, sludgy materials which are difficult to move. In such a case one appropriately feeds back enough of the liquid drainage from the following filtration stage into the concentrated mother liquor enriched with water until the concentration of the dissolved constituents no longer exceeds 15 percent.

in order to separate a predetermined part of the constituents, the concentrated mother liquor enriched with water is slowly cooled with stirring, for instance within two hours, down to about 10°–30° C, preferably to 15°–25° C. Thereby the valuable constituents (DMT, MMT, traces of TPA) that may be fed back into the esterification crystallize out. The interfering intrmediary products and contaminations (TPAA methylester, TA methylester, BA methyleste, heavy metal salts) on the other hand, remain dissolved. Particularly favorable results are obtained when the clear solution at 70°–80° C is poured into a stirrer already holding a precipitation solution at 15°–25° C containing DMT, MMT, and TPA crystals (seeding effect).

Particularly clean separation of the two groups of substances assumes, exactly as for the easy separation of the crystallizate, observing the required conditions of concentration, temperature and specific gravity. If for instance one exceeds the upper limit of specific gravity, one obtains not only a relatively poorly separable crystallizate, but at the same time the TPAA methyl ester content in this crystallizate is appreciably increased. Inversely, when the lower boundary value is passed downward, there is a marked increase in the solubility of DMT and MMT, involving losses in materials that would be directly fed back into esterification.

The separated substances are removed in manners known per se, for instance by filtering, centrifuging and/or settling and, if desired, as is very appropriate, they are fed back into the esterification stage.

The remaining solution is further recovery processed in advantageous manner in that the methanol is distilled off and the acid and ester-like solids are again placed in the oxidation reaction in order to produce TPA. Preferably the methanol is distilled off in the presence of few alkalies such as soda or sodium hydroxide, so that no acid products are contained that might cause corrosion problems. Thereafter, one proceeds as explained below in connection with the illustrative embodiments.

The process of the present invention surprisingly allows a nearly quantitative recovery of the end products dissolved in the mother liquor or of the intermediary products easily convertible into these end products, interfering side products being easily and simultaneously separable. It is of particular advantage in this respect that recovery is possible in simple equipment made of ordinary steel.

Again, essential advantages exist with respect to recovery in the presence of saponifying conditions per U.S. Pat. No. 3,546,283 in the sense that the main part of the constituents dissolved in the mother liquor (DMT, MMT, traces of TPA) may now be immediately fed back into the esterification reaction, whereas in the prior art recovery processes, the constituents are isolated as a mixture of TPA, TPAA, TA, requiring feedback of the total amount into the oxidation stage.

The process of the present invention is new and unexpected to a special degree. Experience for instance shows that one obtains mostly amorphous or also oily precipitates, which can be removed or purified only at great pains, when solutions of organic substances are precipitated by water enrichment. On the other hand, the precipitation in the process of the present invention is crystalline. This is the more surprising that a mixture of many dissolved substances is involved. But it is extremely unexpected that one suceeds in obtaining simultaneously clean separation into two different groups of substances which are to be further treated.

The process of the present invention is operative both for batch loading and in a continous manner.

BRIEF DESCRIPTION OF THE DRAWING

The drawing appended hereto is a flow sheet showing an embodiment of the present invention wherein the preferred, continuous operation is illustrated.

DESCRIPTION OF THE PREFERRED EMBODIMENT

With particular reference to the drawing, mother liquor obtained from an esterification stage and containing about 1.0 to 6.0 percent of solids per kg of solution and about 7 – 13 percent of water is introduced via line 1 into jacket heated stirrer 2. The amount introduced depends on the temperature of the solution in stirrer 2, which is kept at approximately 72°–80° C. Simultaneously, the specific gravity is set for 0.90 – 0.93. Methanol is driven off at this temperature and introduced via line 2a in the subsequent methanol column 13. The methanol vapor flow contains water, minute amounts of BA methylester, TA methylester, also traces of DMT and methylacetate. The concentrated and fully clear solution at 70°–80° C from stirrer 2 in proportion to the supply of mother liquor (1) is continously fed to the subsequent stirrer 3 which is equipped with an evaporation cooler 4, this solution being cooled to 20°–25° C. At this temperature, mostly DMT, MMT and traces of TPA precipitate in crystalline and rapidly settling form. The mixture is transferred via line 5 and pump 6 to centrifuge 7 (full jacket or full scale centrifuge). Continuous separation of the solids (DMT, MMT, traces of TPA) containing about 30 – 40 percent residual humidity takes place at this location. The solid is discarded into container 8 and molten in the following containr 9, the adhering liquid being simultaneously evaporated and fed back via line 9a into the process (distillation or esterification). The molten product is put into esterification via line 10. The liquid drainage from centrifuge 7 is collected in container 11 and from there is fed via line 12 into the methanol dehydration column 13. Water-free methanol is distilled off in column 13. Distillation of this aqueous methanol containing esters, also traces of methylacetate, takes place under saponifying conditions (addition of NaOH via lines 12b/13b), ordinary steel being suitable for the column.

The aqueous-alkaline sump drainage of the methanol column 13 (sodium salts of BA, TA, TPAA, TPA and heavy metal salts) is continuously fed to stirrer 14 and acidified with mineral acid (for instance sulfuric acid) from line 14a, the two organic acids precipitating. In the following filter 15 (for instance a rotary cell filter), the precipitated acid mixture is separated and washed with sufficient hot water until the excess mineral acid, the mineral acid salts and the relatively easily soluble benzoic acid was washed out. If necessary or desired the discarded filter cake is mashed with water and heated to above 100° C under pressure (16), to be filtered and washed again upon cooling. The solid consisting of TPAA, TPA and TA may be fed back into the esterification stage following arbitrary oxidizing pretreatment, or it may also be immediately put into the p-xylol oxidation stage.

If the mother liquor at 1 were to contain less than 7 percent water, water will be continuously fed into the mother liquor supply line 1 via line 1a. If on the other hand the concentration of precipitated solid in container 3 exceeds 15 percent, the liquid drainage of centrifuge 7/container 11 is fed back into stirrer 3 until the concentration of undissolved solids becomes less than 15 percent.

The following specific examples are carried out to further illustrate embodiments of the invention.

EXAMPLE 1

2000 ml (=1,666 gm) of a mother liquor obtained from the esterification of powdered TPA with methanol in the vapor phase in the presence of bulk $SiO_2$, for instance per U.S. Pat. Nos. 3,617,226 and 3,607,044 are put into a 4-liter stirring flask with drop funnel, heating bath and themometer.

This mother liquor, that is, the liquid drainage from the DMT filtration stage and with a $CH_3OH:H_2O$ ratio of 87:13, is of 0.833 specific gravity.

37 gm of solid of the following analytical composition are contained per 1000 gm of mother liquor:

| | |
|---|---|
| TPAA/TPAA methylester | 8 percent by weight |
| BA/BA methylester | 10.2 percent by weight |
| TA/TA methylester | 16.6 percent by weight |
| DMT/MMT/TPA | 65.2 percent by weight |

The solution is heated to about 70° C while stirring and 1,232 gm of $H_2O$ are added dropwise within 10 minutes. The specific gravity of the solution is 0.905 for a weight ratio of methanol: water of 50:50. Upon cooling to about 20° C, a white, crystalline, rapidly settling precipitate is obtained. The precipitated product is sucked off and dried. 33 gm of dry product of the following composition have been obtained:

| | |
|---|---|
| TPAA/TPAA methylester | 0.315 percent |
| BA/BA methylester | 0.2 |
| TA/TA methylester | 0.2 |
| DMT/MMT/TPA | 99.3 |

Operating cautiously, the filtrate solution is concentrated to dryness. 28 gms of solids are isolated, the analytical composition (gas chromatography) being:

| | |
|---|---|
| TPAA/TPAA methylester | 42.3 percent |
| BA/BA methylester | 14.1 |
| TA/TA methylester | 5.1 |
| Intermediate runs | 0.1 |
| DMT, MMT, TPA | 36.3 |
| Last run (3 components) | 2.1 |
| Heavy metal | 0.57 |

This means that when the mother liquor is recovery processed under the above-described conditions, more than 54 percent (33 gm) of the dissolved constituents (61.7 gm) will be precipitated. Of particular interest in this regard is the high proportion, 80 percent (33 gm) of the valuable substances (40.2 gm) contained in the mother liquid, i.e., DMT/MMT/TPA, which may be fed back by means of this precipitation into the esteification process. The interfering intermediate and side products simultaneously being separated, the precipitate may be fed back into the esterification stage immediately without need for purification, so that the yield of the overall process is appreciably increased.

If in lieu of a weight ratio of methanol:water = 50:50 (specific gravity of 0.905) a weight ratio of 25:75 (specific gravity of 0.946) or of 16.5:83.5 (specific gravity of 0.956) is set, the following results are obtained:

| | | |
|---|---|---|
| Precipitate weight ratio $CH_3OH:H_2O$ | 25.1:74.9 | 16.5:83.5 |
| Specific gravity | 0.946 | 0.956 |
| Crystallizate | settling slowly | settling very slowly |
| solids (gm) | 36.7 | 40.0 |
| Solid analysis | | |
| TPAA/TPAA methylester | 1.13 percent | 1.30 percent |
| BA/BA methylester | 0.2 | 0.2 |
| TA/TA methylester | 0.2 | 0.2 |
| DMT/MMT/TPA | 98.47 | 98.2 |

Recovery by distillation of the above filtrated solutions takes place on one hand to recover the methanol and on the other hand to isolate the dissolved constituents in the filtrate solution. It is performed according to the procedure explained in the description of the flow sheet. In this instance, the precipitation occuring because of the addition of relatively large amounts of water, fairly large reaction volumes must be heated up. This drawback may be eliminated by the procedure described in Example 2.

EXAMPLE 2 (See Drawing)

A mother liquor obtained from the esterification of powdered TPA with methanol in the vapor state in the presence of bulk $SiO_2$, for instance per the process of U.S. Pat. Nos. 3,617,226 and 3,607,044 and containing in addition to 12 – 13 percent water mostly DMT, MMT and TPA, plus the methylesters of TPAA, BA and TA and traces of methylacetate, the total concentration of these constituents being about 3.5 percent, is fed via line 1 at a rate of 200 liters an hour into the jacket heated stirrer 2 and heated to about 75° C. 173 liters of the low boiling point components are driven off per hour. The vapor flow consisting of 95 percent methanol; 4.95 percent water; 0.03 percent BA methylester; 0.02 percent methylester; traces of DMT and methylacetate, is fed into column 13. Under these conditions, the specific gravity of the concentrated, wholly clear solution is 0.928. In proportion to the mother liquor supply, the concentrated solution in stirrer 2 at a rigorously kept density is fed via a level control device into cooling stirrer 3. 24.3 percent of constituents are dissolved in the concentrated solution at 75° C.

When cooling to 20° C, 93.5 percent of the constituents precipitate, that is, the concentration of solids in the concentrated mother liquor would amount to 22.6 percent. Therefore 20.5 liters (19.0 kg) of the filtrate drainage of specific gravity 0.928 must be simultaneously fed from container 11 via line 12a into cooling stirrer 3 with the concentrated, hot solution from stirrer 2. Thereby the solid concentration in the concentrated mother liquor is kept to about 13 percent. The solution is cooled in known manner in stirrer 3 to 20° C by evaporation cooling. A white, relatively coarse crystalline precipitate is obtained, which settles rapidly. The mixture is fed via line 5 by means of pump 6 into the continuously operating centrifuge 7. The solid discard from this centrifuge has a residual humidity of about 30 – 40 percent (container 8). Drying of this humid solid may occur for instance by melt drying (stirrer 9), the emanating vapors being fed back into distillation or esterification. 4.8 kg of dry material of the following composition are obtained per hour:

| | | |
|---|---|---|
| TPAA/TPAA methylester | 1.3 | percent |
| BA/BA methylester | 0.25 | percent |
| TA/TA methylester | 0.20 | percent |
| DMT | 27.24 | percent |
| MMT | 65.90 | percent |
| TPA | 5.0 | percent |
| Heavy metal | 0.01 | percent |

There is 93 percent direct recovery in this precipitation stage referred to the total content of the proportions of DMT, MMT and TPA dissolved in the input mother liquor. The content in TPAA and TPAA methylester in the precipitate corresponds to 17.5 percent of the total content of these components in the mother liquor. This means that by far the largest part of the especially interfering TPAA and TPAA methylester is separated, so that the precipitated product may be immediately fed back into the esterification process.

The liquid drainage from centrifuge 7 (27 liters an hour) is fed from container 11 via line 12 into column 13. As already indicated above, about 173 liters an hour of the methanolic vapor flow are fed in parallel from stirrer 2 via line 2a into this column. Ester and among others traces off methylacetate being present besides water in both methanol flows, recovery by distillation in conformity with the process of U.S. Pat. No. 3,546,283 is carried out in the presence of slight amounts of dilute (2–6 percent) sodium hydroxide solution supplied through lines 12b/13b, these amounts sufficing for saponifying the esters. For those saponifying recovery conditions, distillation takes place in a column made of ordinary steel. The two methanolic product flows 2a/12 are selectively combined in a mixing and condensing chamber 2c prior to entry into the distillation column via lines 2a/12 and may be reacted with dilute NaOH solution via line 12b and thereby be subjected to saponifying pre-treatment corresponding to U.s. Pat. No. 3,546,283.

Water-free methanol is obtained above the head of column 13, while an aqueous solution of the sodium salts is withdrawn from the sump and fed into container 14. By acidifying with mineral acid (for instance sulfuric acid) through line 14a, one obtains precipitation of the organic acids. The acid mixture is then separated in the following filter 15, then washed for removal of the excess mineral acid and mineral acid salts, and if desired or required, dried. 1.3 gm of dry materials of the following composition are obtained per hour:

| | |
|---|---|
| TPA | 46.8 percent |
| TPAA | 25.0 percent |
| TA | 12.3 percent |
| Intermediate runnings | 0.6 percent |
| BA | 11.3 percent |
| Terminal runs | 1.0 percent |

By thoroughly washing with hot water, and if necessary also by means of heating under pressure, the benzoic acid may be wholly removed from the acid mixture mashed with water. The acid mixture may be immediately fed back into the oxidation stage. However, the aqueous alkaline sump drainage may also be selectively subjected to oxidation treatmet with sodium hypochlorite, $H_2O_2$, $KMnO_4$ etc. prior to the precipitation stage. The subsequent precipitated, washed and dried product then may be fed back into esterification.

EXAMPLE 3

When powdered TPA is esterified with methanol in the vapor state in the presence of bulk $SiO_2$ and following separation of the crystallized out dimethylester, one obtains a mother liquor with a methanol:water weight ratio of 96:4. Such a mother liquor with low water content necessarily is formed when the total DMT yield in esterification is markedly reduced. Because the water content in this mother liquor is appreciably reduced, the proportion of dissolved solids will also remain relatively high under these conditions.

When this mother liquor is concentrated in stirrer 2, most of the water is removed with the methanol vapor stream, so that the amount of water in the remaining solution will not suffice to adjust the specific gravity (0.90 – 0.93) required by the invention, unless a practically total concentration be undertaken, whereby however the precipitation and simultaneous separation of the interfering side and intermediate products would become unfeasible.

As regards this instance, for an hourly supply of 200 liters of mother liquor through line 1, at least 8 liters of $H_2O$ are supplied via line 1a. When 9 liters of $H_2O$ are supplied per hour, the conditions for recovery such as indicated in Example 2 are set.

We claim:
1. In a process for the preparation of dimethyl terephthalate comprising the steps of esterifying with excess methanol a crude terephthalic acid containing as impurities terephthaldehyde acid, acetic acid and toluic acid to obtain a solid phase of crystallized high purity dimethylterephthalate and predominantly methanolic mother liquor containing minor quantities of dissolved dimethyl terephthalate, monomethyl terephthalate, methyl ester of terephthaldehydic acid, methyl ester of toluic acid, and methyl acetate; separating said crystallized high purity dimehyl terephthalate from said mother liquor, the improvement comprising adjusting said separated mother liquor containing esterification water and about 1.0 to 6.0 percent by weight dissolved solids to a specific gravity of about 0.85 to 0.98 by addition of water to the mother liquor and by evaporation of methanol from the mother liquor at a temperature of about 65°–85° C, cooling said separated mother liquor to a temperature of about 10°–30° C to precipitate said solids and separating said solids from a twice separated mother liquor.

2. The process of claim 1, wherein said solids are recycled to said esterifying step.

3. The process of claim 2, wherein said twice separated mother liquor is distilled off to remove methanol and the sump product is recycled.

4. The process of claim 3, wherein said twice separated mother liquor contains at least 5 percent by weight of water.

5. The process of claim 2, wherein said twice separated mother liquor is reacted at about 50°–150° C for about 5 – 100 minutes with dilute aqueous alkali hydroxide solution and the resulting saponification mixture is distilled into methanol and aqueous salt solution.

6. The process of claim 5, further comprising the step of adding mineral acid to said aqueous salt solution to precipitate crude terephthalic acid.

7. The process of claim 1, wherein said separated mother liquor is adjusted to a specific gravity of about 0.88 to 0.95.

8. The process of claim 1, wherein said separated mother liquor is adjusted to a specific gravity of about 0.90 to 0.93.

9. The process of claim 1, wherein said separated mother liquor has substantially the following composition in weight percent:

|  |  |
|---|---|
| Methanol | 88.73 |
| Water | 7.50 |
| Terephthalic acid dimethyl ester | 0.45 |
| Terephthalic acid mono methyl ester | 1.85 |
| Terephthaladehydic acid methyl ester | 0.70 |
| Toluic acid methyl ester | 0.20 |
| Benzoic acid | 0.02 |
| Acetic acid methyl ester | 0.05 |
| Unknown | 0.50 |
|  | 100.00 |

10. The process of claim 1, wherein said separated mother liquor has substantially the following range of composition in weight percent:

|  |  |
|---|---|
| Methanol | 79 to 94 |
| Water | 5 to 15 |
| Terephthalic acid dimethyl ester | 0.20 to 1.20 |
| Terephthalic acid monomethyl ester | 0.30 to 1.90 |
| Terephthaldehydic acid methyl ester | 0.15 to 0.90 |
| Toluic acid methyl ester | 0.08 to 0.48 |
| Benzoic acid methyl ester | 0.01 to 0.48 |
| Acetic acid methyl ester | 0.01 to 0.06 |
| Unknown | 0.25 to 0.98. |

11. The process of claim 10, wherein said solids separated from a twice separated mother liquor have substantially the following range of composition in weight percent:

|  |  |
|---|---|
| Terephthalic acid plus esters | 93.5 to 99.8 |
| Terephthaldehydic acid methyl ester | 0.05 to 3.3 |
| Toluic acid methyl ester | 0.07 to 1.2 |
| Benzoic acid methyl ester | 0.05 to 1.0 |
| Unknown | 0.03 to 1.0. |

12. The process of claim 11, wherein said twice separated mother liquor has the following composition range in weight percent:

|  | Range |
|---|---|
| Methanol | 21.0 – 72.6 |
| Water | 22.4 – 77.0 |
| Terephthalic acid plus esters | 0.20 – 1.5 |
| Terephthaldehydic acid plus ester | 0.15 – 0.9 |
| Benzoic acid plus ester | 0.14 – 1.5 |
| Toluic acid plus ester | 0.10 – 1.3 |
| Heavy metal | 0.01 – 0.4. |

13. In a process for the preparation of dimethyl terephthalate comprising the steps of esterifiying with excess methanol a crude terephthalic acid containing as impurities terephthaldehyde acid, acetic acid and toluic acid to obtain a solid phase of crystallized high purity dimethylterephthalate and predominantly methanolic mother liquor containing minor quantities of dissolved dimethyl terephthalate, monomethyl terephthalate, methyl ester of terephthaldehydic acid, methyl ester of toluic acid, and methyl acetate; separating said crystallized high purity dimethyl terephthalate from said mother liquor, the improvement comprising adjusting said separated mother liquor containing esterification water and about 1.0 to 6.0 percent by weight dissolved solids to a specific gravity of about 0.85 to 0.88 by evaporation of methanol from the mother liquor at a temperature of about 65°–85° C, cooling said separated mother liquor to a temperture of about 10°–30° C to precipitate said solids and separating said solids from a twice separated mother liquor.

14. The process of claim 13, wherein said solids are recycled to said esterifying step.

15. The process of claim 14, wherein said twice separated mother liquor is distilled off to remove methanol and the sump product is recycled.

16. The process of claim 15, wherein said twice separated mother liquor contains at least 5 percent by weight of water.

17. The process of claim 14, wherein said twice separated mother liquor is reacted at about 50°–150° C for about 5 – 100 minutes with dilute aqueous alkali hydroxide solution and the resulting saponification mixture is distilled into methanol and aqueous salt solution.

18. The process of claim 17, further comprising the step of adding mineral acid to said aqueous salt solution to precipitate crude terephthalic acid.

19. The process of claim 13, wherein said separated mother liquor is adjusted to a specific gravity of about 0.88 to 0.95.

20. The process of claim 13, wherein said separated mother liquor is adjusted to a sepcific gravity of about 0.90 to 0.93.

21. The process of claim 13, wherein said separated mother liquor has substantially the following range of composition in weight percent:

| | |
|---|---|
| Methanol | 79 to 94 |
| Water | 5 to 15 |
| Terephthalic acid dimethyl ester | 0.20 to 1.20 |
| Terephthalic acid monomethyl ester | 0.30 to 1.90 |
| Terephthaldehydic acid methyl ester | 0.15 to 0.90 |
| Toluic acid methyl ester | 0.08 to 0.48 |
| Benzoic acid methyl ester | 0.01 to 0.48 |
| Acetic acid methyl ester | 0.01 to 0.06 |
| Unknown | 0.25 to 0.98. |

22. The process of claim 21, wherein said solids separated from a twice separated methoer liquor have substantially the following range of composition in weight percent:

| | |
|---|---|
| Terephthalic acid plus esters | 93.5 to 99.8 |
| Terephthaldehydic acid methyl ester | 0.05 to 3.3 |
| Toluic acid methyl ester | 0.07 to 1.2 |
| Benzoic acid methyl ester | 0.05 to 1.0 |
| Unknown | 0.03 to 1.0. |

23. The process of claim 22, wherein said twice separated mother liquor has the following composition range in weight percent:

| | |
|---|---|
| Methanol | 21.0 – 72.6 |
| Water | 22.4 – 77.0 |
| Terephthalic acid plus esters | 0.20 – 1.5 |
| Terephthaldehydic acid plus ester | 0.15 – 0.9 |
| Benzoic acid plus ester | 0.14 – 1.5 |
| Toluic acid plus ester | 0.10 – 1.3 |
| Heavy metal | 0.01 – 0.4. |

* * * * *